United States Patent [19]

Garfinkel

[11] Patent Number: 5,577,911
[45] Date of Patent: Nov. 26, 1996

[54] ULTRASONICALLY DRIVEN CURETTE FOR PERIODONTAL CURETTAGE

[76] Inventor: Leonard M. Garfinkel, 3050 N. 35th St., Hollywood, Fla. 33021

[21] Appl. No.: 150,263

[22] Filed: Nov. 9, 1993

Related U.S. Application Data

[63] Continuation of Ser. No. 608,671, Oct. 18, 1990, abandoned, which is a continuation of Ser. No. 825,883, Feb. 4, 1986, abandoned.

[51] Int. Cl.⁶ .............................. A61C 1/07; A61C 3/03; A61C 3/08
[52] U.S. Cl. .............................. 433/119; 433/215
[58] Field of Search .................... 433/114, 118, 433/119, 165, 215, 216

[56] References Cited

U.S. PATENT DOCUMENTS

| | | | |
|---|---|---|---|
| 2,874,470 | 2/1959 | Richards | 433/165 |
| 3,763,411 | 10/1973 | Goof | 433/119 |
| 3,924,335 | 12/1975 | Balamuth et al. | 433/119 |
| 3,930,173 | 12/1975 | Banko | 433/119 X |
| 4,283,175 | 8/1981 | Nash | 433/165 |
| 4,353,696 | 10/1982 | Bridges | 433/119 X |
| 4,370,131 | 1/1983 | Banko | 433/119 X |
| 4,731,019 | 3/1988 | Martin | 433/119 |
| 5,188,531 | 2/1993 | Von Sutfin | 433/119 X |
| 5,236,358 | 8/1993 | Sieffert | 433/119 |

OTHER PUBLICATIONS

"Dental Instruments", C. V. Mosby Published 1981, pp. 128, 129, 130.

Primary Examiner—Nicholas D. Lucchesi
Attorney, Agent, or Firm—Malin, Haley, DiMaggio & Crosby

[57] ABSTRACT

This invention relates to a periodontal instrument and curettage method for separating and removing diseased granulation tissue from a periodontal cavity. The instrument is comprised of a periodontal curette affixed to a source of ultrasonic energy that drives the curette in an elliptical motion at an ultrasonic frequency. The instrument greatly reduces the physical effort and time required for periodontal curettage.

5 Claims, 2 Drawing Sheets

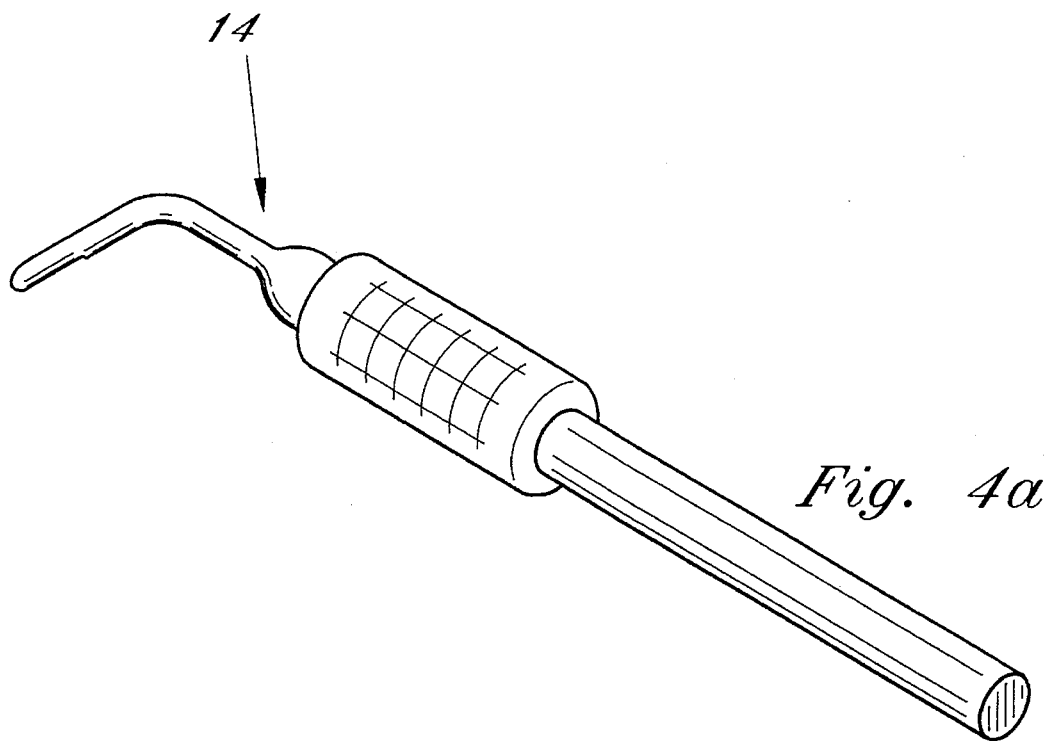
Fig. 4a
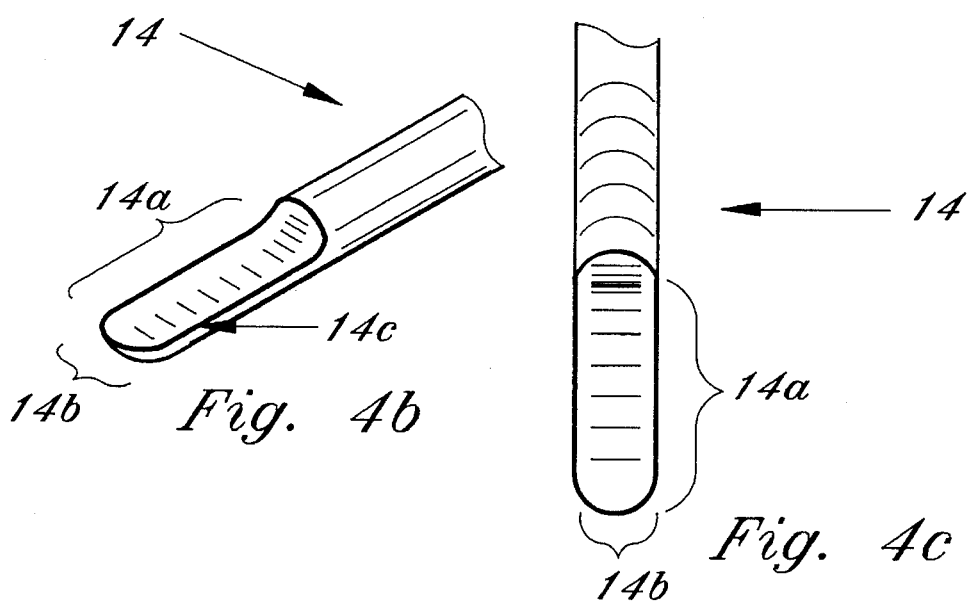
Fig. 4b
Fig. 4c
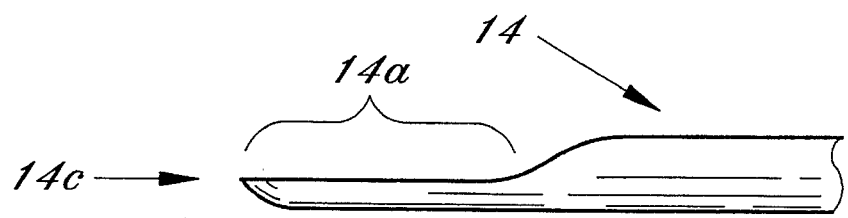
Fig. 4d

ULTRASONICALLY DRIVEN CURETTE FOR PERIODONTAL CURETTAGE

This is a continuation of application Ser. No. 07/608,671 filed on Oct. 18, 1990, now abandoned, which is a continuation of application Ser. No. 06/825,883, filed Feb. 4, 1986, now abandoned.

BACKGROUND OF THE INVENTION

1. Field of the Invention

This invention relates generally to a periodontal surgical instrument for the removal of diseased tissue from periodontal pockets, and specifically to an ultrasonically vibrated curette that is used in periodontal curettage to separate and remove granulation tissue from surrounding bone tissue and in between adjacent teeth.

Periodontitus is a human gum disease characterized by the formation of periodontal pockets (deep spaces) between the gum and tooth resulting in the reduction of attachment between soft tissue and the tooth (bone loss). The pockets accumulate diseased tissue, termed "granulation" tissue.

Initial periodontal therapy is the meticulous removal of granulation tissue as well as inflamed gingival tissue residing in the periodontal pocket formed by surrounding healthy bone tissue and tooth. Conventionally, in recent years, the removal of granulation tissue has been accomplished by manual curettage by a periodontist or general dentist doing periodontal therapy.

The scraping action employed in periodontal curettage that separates the diseased granulation tissue or inflamed periodontal tissues from healthy bone tissue is completely different than surgical cutting that mechanically divides tissue when cut with a sharp blade. In fact, in periodontal curettage it is important that healthy bone tissue not be cut away because preservation of as much healthy bone tissue is important for firm tooth support. Also it is important that the instrument not have square edges that would gouge or cut into the roots of adjacent teeth or get caught in softer bony tissue.

The manual scraping action of the periodontist using a curette is physically strenuous because of the physical effort required in separating the sinewy diseased and healthy tissues and the numerous, awkward manual positions of the curette necessitated by the restricted accessibility of periodontal pockets. By virtue of the numerous periodontal cavities in an average patient, periodontal curettage is also not only strenuous but time consuming, requiring stamina.

The invention described herein has been found to greatly reduce the physical effort and time required for periodontal curettage. The invention utilizes an ultrasonically vibrated curette that efficiently separates diseased granulation tissue from surrounding healthy bone tissue or in between or surrounding adjacent teeth in a periodontal cavity for expeditiously voiding a periodontal pocket without traumatizing healthy bone tissue.

2. Description of Related Art

Ultrasonic energy has been conventionally used for cleaning the hard enamel of tooth surfaces for quite some time.

Surgical tools for cutting tissue have also been employed that utilize knife blades or sharp cutting edges that are mechanically vibrated at ultrasonic frequencies. An ultrasonic cutting tool is shown in U.S. Pat. No. 2,990,616 issued Jul. 4, 1961 to Balamuth et al. Here a tool is described for the cutting of a desired hole in a tooth. Since the shape of the hole demands that it be barlike in nature, all of the described art has right angles to achieve this shape. The tools are end cutting to be used similar to a wood chisel. The design of the instrument is to cut into a homogenious material and create a certain preconceived shape. Another Balamuth tool for removing tissue is shown in U.S. Pat. No. 3,526,219 issued Sep. 1, 1970. Here the inventor describes a method for the systematic removal of superficial layers of tissue using a microchopping principle. The instrument must be moved parallel to the plane of the tissue so as to not gouge the underlying tissue. The removal of individual layers and the specific need to work the instrument parallel to the plane of the tissue make it impossible to be used where the removal of tissue from a bony cavity are concerned. A vibratory surgical instrument is disclosed in U.S. Pat. No. 2,714,890 issued to Vang on Aug. 9, 1955. Here the inventor describes a blade to be used in conjunction with ultrasonic vibration to enhance the cutting action of the blade. The purpose of the blade as described is to separate tissue with a cutting action. It would be impossible for the operator to actually remove tissue with such an instrument. Balamuth et al. discloses an ultrasonically vibrated cutting knife in U.S. Pat. No. 3,086,288 issued Apr. 23, 1963. All of these devices have as a primary objective to provide a cutting action and thus are unsuitable for periodontal surgery.

SUMMARY OF THE INVENTION

A method and apparatus for periodontal curettage including separating and removing diseased granulation tissue from healthy tissue in a periodontal pocket or cavity. The apparatus is comprised of a curette sized for utilization in a periodontal cavity rigidly affixed to a source of ultrasonic energy, encased in a housing that can be manually grasped and manipulated by the periodontist. The curette body is a rigid shaft having a spoon-shaped end portion with a rounded tip and sharp edges. The curette shaft is rigidly attached to a member that is ultrasonically vibrated, preferably at 25,000 Herz. The vibration is elliptical or longitudinal, with the amplitude being between 0.001 inches and 0.003 inches.

The longitudinal shaft configurations of the curette bodies may vary angularly between the curette tip and the shaft axis for enhancing accessibility of the curette tips to extremes of the periodontal pocket base.

The ultrasonic energy may be provided by a magnetostrictive, piezoelectric or electrodynamic transducer mounted in a suitable housing.

The method of the invention is comprised of the steps of ultrasonically vibrating a periodontal curette, introducing the vibrating curette into a periodontal pocket containing diseased granulation tissue, scraping the pocket walls with the vibrating curette and voiding the separated diseased tissue from the pocket.

It is an object of this invention to reduce the physical effort and time required to remove diseased tissue from a periodontal cavity.

It is another object of this invention to increase the efficiency in periodontal curettage without increasing trauma or excessive removal of surrounding healthy bone tissue using an ultrasonically driven periodontal curette.

In accordance with these and other objects which will be apparent hereinafter, the present invention will now be described with particular reference to the accompanying drawings.

BRIEF DESCRIPTION OF THE DRAWINGS

FIG. 4a shows a rear perspective view of the invention.

FIG. 4b shows an enlarged fragmentary perspective view of the curette tip utilized in one embodiment of the invention, FIG. 4c is a top plan view of the tip shown in FIG. 4b.

FIG. 4d is a fragmentary side elevational view of the tip shown in FIG. 4b.

PREFERRED EMBODIMENT OF THE INVENTION

Figure 1:
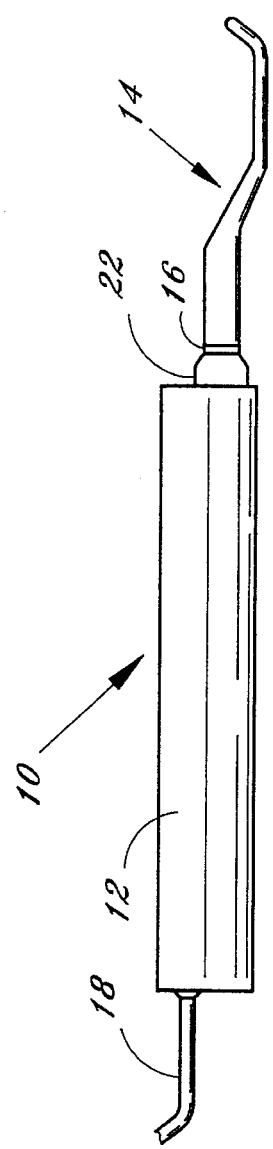
FIG. 1 shows a side, elevational view of the invention.

Referring now to the drawings, and in particular, FIG. 1, the invention is shown generally at 10 comprised of a periodontal curette 14 affixed to a source of ultrasonic energy located in tubular housing 12 that functions as a manual grasping handle. Electrical wires 18 provide a source of electrical energy to the invention 10 from a convention A.C. electrical outlet (not shown).

Figure 2:
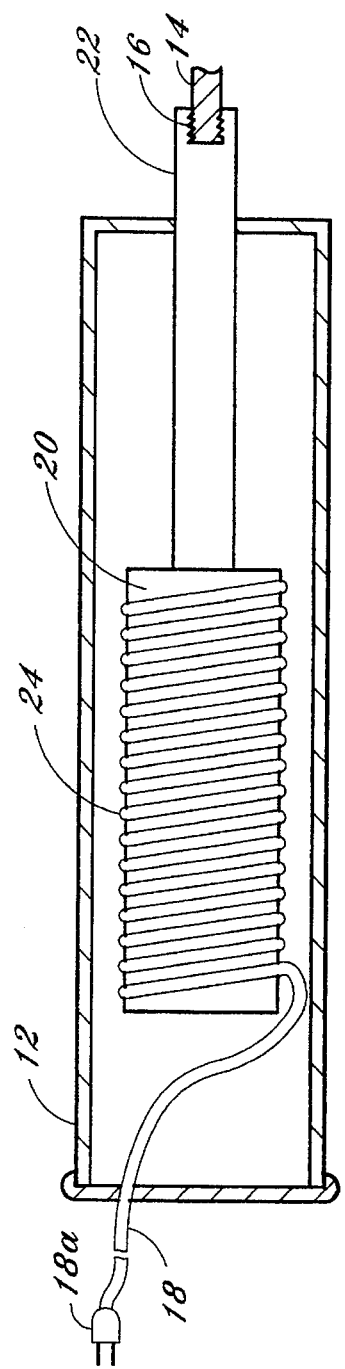
FIG. 2 shows a side, elevation view of the invention in cross-section.

FIG. 2 shows the ultrasonic transducer comprised of a magnetostrictive element 20 surrounded by electrical wiring 24 connected to a source of electrical energy by wires 18. A shaft 22 is rigidly affixed to element 20 to transmit the ultrasonic energy to curette 14 through threaded connector 16, which permits detachment of curette 14 from the transducer. The operation of the ultrasonic transducer is conventional and may also be provided by piezoelectric or electrodynamic sources in lieu of magnetostrictive element 20. The curette is constructed of metal or other suitable material that will receive the ultrasonic vibrations described herein.

Figure 3:
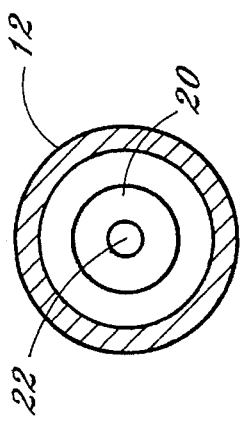
FIG. 3 shows a front elevational view of the invention in cross-section.

FIG. 3 and FIG. 4a show the tubular shape of housing 12 which is sized in diameter to fit comfortably but permitting a firm grip by the periodontist's hand.

FIGS. 4b, 4c and 4d show a typical curette tip used in periodontal curettage having a spoon-shaped portion 14a, a rounded end tip 14b and sharp edges 14c. Various sized and shaped curettes found in periodontal subgingival surgery can be employed with the ultrasonic energy source dependent upon the size and location of the periodontal cavity. The tip of curette 14 has a rounded end 14b. The longitudinal edges 14c are sharp and extend back away from rounded end 14b and form the outside edges of surface 14d which is substantially flat. The exterior surface is semi-circular in cross-section such that the curette tip is spoon shaped in appearance.

In operation, the desired curette 14 is selected and attached to shaft 16. Ultrasonic energy between 18,000–25,000 cycles per second is applied in an elliptical motion to the curette 14, with an amplitude varying from 0.001 inches to 0.003 inches. The vibrating curette is disposed in the periodontal cavity and is used to scrape and remove diseased granulation tissue.

The invention has been found to greatly reduce the physical effort required to separate diseased tissue from the bone tissue, expediting periodontal surgery for both the patient and the periodontist.

What is claimed is:

1. An instrument for separating and voiding a diseased periodontal cavity of granulation tissue in a patient, comprising:

a periodontal curette, said curette comprising an elongated, partially curved rigid member having first and second ends, said first end having an exterior surface that is semicircular in cross section, a rounded end tip, and a unitarily formed spoon-shaped blade, said spoon-shaped blade having a continuous, sharp cutting edge forming said rounded tip, said spoon-shaped blade having a semicircular cross section, and said spoon-shaped blade having a face and lateral sides that meet to form the sharp cutting edge for cutting away said granulation tissue and sized for insertion into a patient's mouth;

means for oscillating said curette at an ultrasonic frequency rigidly connected to said curette at said second end thereof; and means for manually grasping said oscillating means rigidly connected to and integral with said oscillating means whereby said spoon shaped blade associated with said curette may be oscillated at said ultrasonic frequency and contemporaneously inserted into a patient's mouth in the proximity of said diseased cavity so that said granulation tissue may be easily separated and removed.

2. An instrument as in claim 1, further comprising: means for detachably connecting said curette to said oscillating means.

3. An instrument as in claim 1, wherein said ultrasonic frequency oscillates said curette between 18,000 and 25,000 Hertz and comprises a magnetostrictive transducer.

4. An instrument as in claim 1, wherein the amplitude of said ultrasonic oscillation is elliptical and between 0.001 and 0.003 inches.

5. An instrument for separating and voiding a diseased periodontal cavity of granulation tissue, comprising:

a periodontal curette, said curette comprising an elongated partially curved rigid member having first and second ends, said first end having a unitarily formed, sharp cutting blade for cutting away said granulation tissue, said cutting blade comprising a spoon-shaped portion terminating in a rounded end tip and transversely disposed sharp cutting blade edges;

means for oscillating said curette at an ultrasonic frequency between 18,000 and 25,000 hertz at an amplitude of 0.001 to 0.003 inches in an elliptical profile, said means for oscillating comprising a magnetostrictive element having an electrical coil helically wound thereover which may be energized by an external source of electrical energy, said magnetostrictive element being rigidly and removably affixed to said curette at said second end thereof; and means for manually grasping said oscillating means, said means for manually grasping comprising an elongated hollow cylindrical member having a plurality of external surface undulations associated with the exterior thereof, said means for manually grasping coaxially disposed with resect to said oscillating means and rigidly attached thereto, whereby said means for cutting associated with said curette may be oscillated at said ultrasonic frequency and contemporaneously inserted into a patient's mouth in the proximity of said diseased cavity so that said granulation tissue may be easily separated and removed during curettage.

\* \* \* \* \*